United States Patent [19]
Berick et al.

[11] 4,374,620
[45] Feb. 22, 1983

[54] PHOTOMETRIC FLOW CELL

[75] Inventors: Alan C. Berick, Albany; Haakon T. Magnussen, Jr., Pinole, both of Calif.

[73] Assignee: Altex Scientific, Inc., Berkeley, Calif.

[21] Appl. No.: 229,614

[22] Filed: Jan. 29, 1981

[51] Int. Cl.³ ............................................. G01N 1/10
[52] U.S. Cl. ................................................. 356/246
[58] Field of Search ....................... 356/410, 411, 246

[56] References Cited

U.S. PATENT DOCUMENTS

| | | | |
|---|---|---|---|
| 3,515,491 | 6/1970 | Emary | 356/246 |
| 3,647,304 | 3/1972 | Emmel et al. | 356/246 |

FOREIGN PATENT DOCUMENTS

| | | | |
|---|---|---|---|
| 2158220 | 3/1973 | Fed. Rep. of Germany | 356/246 |
| 2246225 | 4/1973 | Fed. Rep. of Germany | 356/246 |
| 458794 | 8/1968 | Switzerland | 356/246 |
| 2001752 | 2/1979 | United Kingdom | 356/246 |

*Primary Examiner*—John K. Corbin
*Assistant Examiner*—Matthew W. Koren
*Attorney, Agent, or Firm*—R. J. Steinmeyer; Robert R. Meads; John R. Shewmaker

[57] ABSTRACT

A photometric flow cell for high pressure liquid chromatography having an illuminated passageway therein between open ends of which fluid samples are flowed for analysis. An annular, porous flow impedance element is supported in an annular channel surrounding one end of the passageway. The impedance element reduces turbulence of flow through the open end by evenly distributing the flowing fluid circumferentially about the end opening.

13 Claims, 3 Drawing Figures

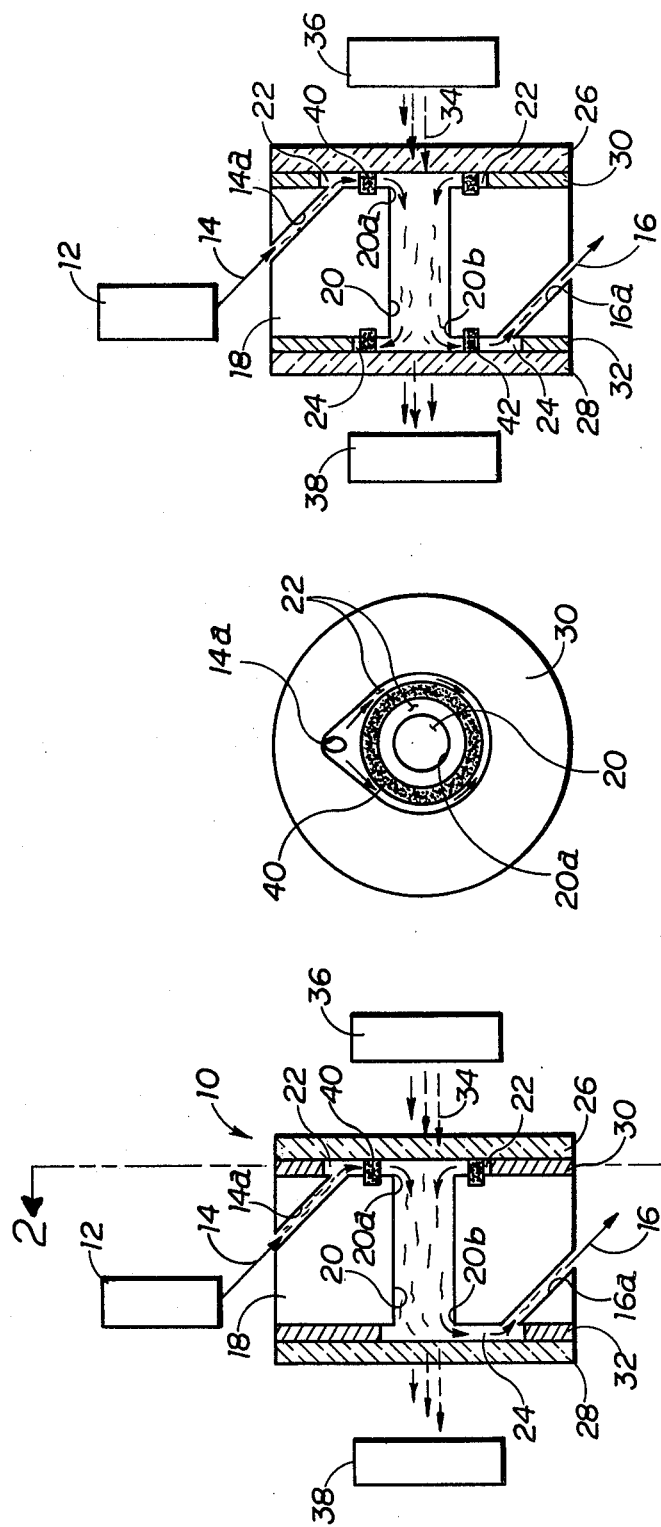

PHOTOMETRIC FLOW CELL

BACKGROUND OF THE INVENTION

1. Field of the Invention

The present invention relates generally to the analysis of fluid samples and, more particularly, to the analysis of fluid samples in a photometric flow cell. The invention is particularly suited for use in liquid chromatography in which a stream of successive fluid sample fractions eluted from a chromatographic column is flowed through a photometric cell for analysis.

2. Description of the Prior Art

Numerous photometric flow cells have been developed for measuring optical properties of fluid samples flowed through cells. Typically, a flow passageway of the cell is bounded at opposite ends by optically transparent windows which permit a light beam to be directed into one end, along the length of, and out the other end of the flow cell passageway. Conduits connected to entrance and exit openings of opposite ends of the passageway provide for introduction of fluid at one end and for removal of fluid at the other end of the passageway. A light detector intercepts light exiting the flow cell to provide a measure (usually absorbance) of the effect of the sample on the light. From this measurement quantitative and qualitative information regarding the sample is derived.

Flow cells of the foregoing nature can be grouped generally as either static or dynamic. In a static flow cell, the photometric light measurement is performed with the fluid sample at rest in the flow cell passageway. In a dynamic flow cell, on the other hand, the photometric measurement is made as the sample is flowing through the passageway. As a result, dynamic flow cells are particularly prone to measurement errors from turbulence or other disruptions in the flowing sample.

In high-pressure liquid chromatography (HPLC) sample analysis in dynamic flow cells is complicated by the fact that measurements are made on flowing samples which are minute in volume and which are flowed through the cell at high pressure. In this respect, HPLC sample fractions (carried in a solvent matrix) are typically between 30 $\mu$l-1.0 ml in volume and are flowed at rates between 0.5-2.0 ml/min at pressures between 100-300 atmospheres through conduits as small as 0.25 mm inside diameter. In order to minimize spreading of sample within the solvent matrix, the sample volume is minimized and the conduit connecting the chromatographic column and the flow cell is configured to have minimum length (i.e. several inches) and interior diameter. For such applications, a representative flow cell is typically dimensioned with a flow passageway 1.0 cm in length and between 1.0-2.0 mm inside diameter to define a total flow passage volume of about 10-20 $\mu$l.

With such dimensional restrictions as above, it is imperative in HPLC applications that the flow of sample fractions through the flow cell approach plug flow, i.e. flow such that each minute sample fraction is retained as a discrete fluid segment all portions of which travel at the same velocity with a flat front and for which mixing between successive segments is avoided. Unfortunately, ideal plug flow is difficult to attain in practice. Such is caused in part by the geometry of the flow cell passageway and the conduits which deliver and remove the sample fractions. In this regard, an abrupt and turbulent flow transition is created by the relatively narrow diameter conduit opening into one end of the wider diameter flow passageway. Fluid flowed through the conduit into and through the entrance opening of the passageway follows the path of least resistance through only one side of the passageway opening, and turbulence is created in the entering fluid as it then spreads out across the flow passageway. Because of such turbulence, the flow cell exhibits several problems in operation including: (1) instability in the optical baseline between measurement of successive fluid fractions, particularly fluids of differing indices of refraction, (2) mixing between successive fractions, (3) formation of air bubbles in the flow cell passageway, and (4) formation of dead pockets or corners in the flow passageway which require relatively large volumes of fluid (e.g. 2-3 cell volumes) to totally sweep or flush each sample from the passageway. A turbulent transition at the exit opening of the flow passageway can cause similar problems.

Accordingly, a need exists for a flow cell adapted for dynamic optical measurement of continuously flowing fluid sample without the drawbacks of the prior art. The present invention meets these needs.

SUMMARY OF THE INVENTION

The present invention resides in an arrangement for controlling sample flow through a flow cell in a manner which overcomes the drawbacks of the prior art. The invention eliminates the abrupt transition for fluid flow at the entrance, at the exit, or at both entrance and exit of the flow passageway of the cell. The improved flow cell is achieved in a commercially practical form which is simple and inexpensive in construction and reliable in operation.

To the foregoing ends, the present invention is embodied in a flow cell of the type comprising a passageway through which a fluid sample is flowed for analysis between entrance and exit ends thereof. Optically transparent windows adjacent the ends of the passageway permit the passage of light energy along an optical path through the flowing fluid sample. Applicants have discovered that a flow impedance element surrounding the entrance end of the passageway (or surrounding the exit end of the passageway, or both) and distributing fluid flow circumferentially through the open end of the passageway about the entire peripheral edge thereof will produce even flow of fluid into (and/or out of) the flow cell passageway and virtually eliminate the turbulent flow transition in the prior devices.

In a preferred embodiment, the flow impedance element comprises a microporous material such as an open pore stainless steel frit or fluorocarbon plastic. The impedance element is preferably configured as an annulus surrounding the entrance and/or exit ends of the passageway. Further, the element has a pore size establishing a resistance to fluid flow greater than the resistance presented by the flow cell passageway through which fluid is flowed. With such arrangement, fluid is distributed around the annular impedance element and thereby flows through the element and the associated entrance/exit end of the passageway evenly about the periphery of the open end(s).

BRIEF DESCRIPTION OF THE DRAWINGS

FIG. 1 is a cross-sectional view through a flow cell of the present invention as incorporated in an HPLC measuring system and illustrates in block diagram form the optical components associated with the flow cell.

FIG. 2 is a view taken along line 2—2 of FIG. 1 generally perpendicular to the optical axis of FIG. 1.

FIG. 3 is a view similar to FIG. 1 illustrating the impedance element of the invention incorporated at both the entrance and exit openings of the flow cell passageway.

DESCRIPTION OF THE PREFERRED EMBODIMENTS

As shown in the drawing, and particularly FIG. 1 thereof, the present invention is embodied in a photometric flow cell 10 which receives liquid sample fractions flowed under pressure from a high-pressure liquid chromatograph column 12 through a supply conduit 14 and which discharges the fluid sample after analysis through discharge conduit 16. Discharge conduit 16 is connected to a back pressure regulator (not shown) for establishing requisite pressure in the flow path from the column 12 through the flow cell 10. Typically, the discharge conduit is connected to a suitable waste receptacle or sump into which the fluid is flowed.

The flow cell comprises a generally cylindrical body 18 through which a flow passageway 20 is defined between the ends of the body. Fluid supply conduit 14 extends as an internal bore or conduit 14a through body 18 opening into a generally annular channel 22 surrounding the right side opening 20a of passageway 20. Similarly, a corresponding annular channel 24 surrounds the left end opening 20b of passageway 20 and is connected to discharge conduit 16 through internal bore or conduit 16a in body 18.

The ends of flow passageway 20 are closed by optically transmissive windows 26 and 28 respectively sealed to and spaced from body 18 by washers 30 and 32. A clamp (not shown) retains the windows in place on the body 18 in a fluid-tight seal against the washers. An optical path 34 is established between a light source 36 and light detector 38 through the windows 26 and 28 and the flow passageway 20 therebetween.

Thus arranged, sample fractions eluted from chromatograph column 12 are flowed under pressure through supply conduit 14 into annular channel 22 from which they enter the right hand or entrance opening 20a of flow passageway 20. The fluid is flowed through the passageway and out the left hand or exit opening 20b into annular channel 24 and thence out discharge conduit 16 to waste. Optical analysis of the flowing sample fraction is performed in a conventional manner by measuring an optical characteristic of the sample as the sample flows through the passageway. In this regard light source 36 directs light into the passageway along optical path 34, and detector 38 measures the effect of the flowing sample on the light by measuring the light which exits the flow cell.

As described to this point, photometric flow cell 10 is of conventional construction. As indicated previously, fluid sample fractions flowed through cell bore 14a into annular channel 22 follow the path of least resistance into flow passageway 20 entering the flow passageway at the side of the entrance opening 20a closest to bore 14a (top side in FIG. 1). As the fluid is then flowed through the passageway from the top side of the entrance opening, it begins to spread across the width of the passageway until it fills the entire width. During such spreading, fluid will be in a turbulent phase producing the difficulties previously discussed. A similar turbulence results at the exit opening 20b as the exiting fluid, seeking the path of least resistance, flows out of the exit opening at the side of the opening adjacent bore 16a (the bottom side in FIG. 1).

In accordance with a primary aspect of the present invention an impedance means is provided in the flow path through cell 10 for distributing fluid about the periphery of flow passage openings 20a and/or 20b. To this end, referring to FIG. 1, a flow impedance element 40 is formed as an annulus in the channel 22 and encircling the entrance opening 20a to passageway 20. In one embodiment, impedance element 40 is formed of an open-pore, microporous stainless steel frit material of the type commonly employed as a support for packing material in chromatographic columns. The frit is formed by fusing stainless steel beads into a frit having a resistance to fluid flow determined by its pore size. One suitable sintered stainless steel frit for impedance element 40 is sold by Mott Metallurgical Corp., Farmington, CT., 06032 under the name "Hastelloy." Alternatively, a plastic microporous material may be employed for impedance element 40. One suitable fluorocarbon plastic is sold by Glasrock Products Inc., Porex Division, Fairburn, GA, 30213 under the name "Porex."

The opposing annular planar faces of the impedance element 40 are sealed to the mating faces of window 26 and body 18. Preferably, as illustrated, the impedance element is seated within a mating annular recess in the face of body 18. Significantly, as illustrated in FIG. 2, the outer annular diameter of impedance element 40 is less than that of channel 22 such that channel 22 surrounds the radially outward annular surface of the impedance element thereby providing an annular volume of channel 22 communicating with bore 14a and surrounding the periphery of the impedance element.

In accordance with a further aspect of the invention, the resistance of the impedance element 40, as determined by its pore size, is established at a value greater than the flow resistance of passageway 20. A pore size in the range of about $2\mu$ to $10\mu$ is satisfactory for this purpose. With the flow resistance thus established, fluid sample entering annular channel 22 from capillary duct 14a, upon encountering impedance element 40, seeks the path of least resistance within channel 22 and is distributed around the periphery of the impedance element thereby filling the annular channel with fluid. The fluid then passes through all peripheral portions of the impedance element and enters flow cell passageway 20 about all sides of the entrance opening 20a of the passageway. Such uniform distributed introduction of fluid has been found to substantially reduce or eliminate the turbulent phase of fluid introduced into the passageway. As a result, the flow into the passageway approaches ideal plug flow which serves to eliminate the problems of light deflection, baseline instability, air bubble formation, dead volumes, and the like thereby improving optical resolution of the cell and minimizing the sweep-out volume required to flush the sample from the cell.

In accordance with a further aspect of the invention, referring to FIG. 3, an additional impedance element 42, identical to element 40, is provided in annular channel 24 at the exit opening 20b of flow passageway 20. With such an arrangement, further flow stabilization is achieved with the second impedance element which resists the flow through passageway 20 causing fluid to be distributed around the entire inner annular surface of the impedance element. The result is that fluid exits passageway 20 about the entire peripheral edge of the exit opening, passing through the impedance element about its entire periphery into the outer annular section of channel 24 and then exits through bore 16a.

In accordance with a further embodiment, not shown, the impedance element 40 is eliminated from the embodiment of FIG. 3 while retaining the impedance element 42 at the exit opening 20b. The invention thus contemplates incorporation of an impedance element at the entrance opening alone, at the exit opening alone, or at both the entrance and exit openings.

While several preferred embodiments of the invention have been illustrated and described, it will be understood that various modifications may by made therein without departing from the spirit and scope of the appended claims.

What is claimed is:

1. A photometric flow cell comprising:
   a flow cell body having a passageway for receiving and passing fluid samples between opposite ends thereof;
   optically transparent windows at said opposite ends of said passageway for passing light along an optical path through sample in said passageway;
   an annular channel around one of said opposite ends of said passageway; and
   flow impedance means including a microporous annulus in said channel surrounding said one of said opposite ends for circumferentially distributing fluid flowing therethrough.

2. The flow cell of claim 1 including means for flowing said fluid samples into said passageway through said one of said opposite ends.

3. The flow cell of claim 1 including means for flowing said fluid samples out of said passageway through said one of said opposite ends.

4. The flow cell of claim 1 wherein said annular channel and said flow impedance means are provided at each of said opposite ends of said passageway.

5. The flow cell of claim 1 or 4 wherein said microporous annulus has a pore size in the range of about 2.0–10μ.

6. The flow cell of claim 5 wherein said microporous annulus comprises metal.

7. The flow cell of claim 5 wherein said microporous annulus comprises plastic.

8. In combination:
   a flow cell body having a passageway for receiving and passing fluid samples between opposite ends thereof;
   means for measuring a characteristic of fluid sample while in the passageway; and
   fluid flow impedance means including a microporous annulus surrounding one of said opposite ends of said passageway for circumferentially distributing fluid flowing therethrough about the circumference of said one of said opposite ends.

9. The combination of claim 7 wherein said characteristic is measured by said measuring means as said fluid sample passes along said passageway.

10. The combination of claim 8, wherein said flow impedance means are provided at each of said opposite ends of said passageway.

11. The combination of claim 8 or 10 wherein said microporous annulus has a pore size in the range of about 2.0–10.0μ.

12. The flow cell of claim 11 wherein said microporous annulus comprises metal.

13. The flow cell of claim 11 wherein said microporous annulus comprises plastic.

* * * * *